United States Patent [19]

Iwa et al.

[11] Patent Number: 5,681,921
[45] Date of Patent: Oct. 28, 1997

[54] PERFLUOROALKYLENEETHERTRIAZINE OLIGOMER AND PROCESS FOR PRODUCING THE SAME

[75] Inventors: Riichi Iwa, Kitaibaraki; Haruyoshi Tatsu, Hitachi, both of Japan; Sokolov Sergey Vasilyevich; Kollar Alexander Nikolaevich, both of Saint Petersburg, Russian Federation

[73] Assignees: Nippon Mektron, Limited, Tokyo, Japan; S.V. Lebedev, Saint Petersburg, Russian Federation

[21] Appl. No.: 420,166

[22] Filed: Apr. 11, 1995

[30] Foreign Application Priority Data

Apr. 19, 1994 [JP] Japan .................... 6-103204

[51] Int. Cl.$^6$ .................... C08G 73/00; C08G 73/06
[52] U.S. Cl. .................... 528/362; 528/486
[58] Field of Search .................... 528/362, 486

[56] References Cited

U.S. PATENT DOCUMENTS

| | | |
|---|---|---|
| 3,708,483 | 1/1973 | Anderson et al. . |
| 3,816,416 | 6/1974 | Croft et al. . |
| 3,888,854 | 6/1975 | Schuman et al. . |
| 4,102,872 | 7/1978 | Griffin .................... 528/362 |
| 4,234,715 | 11/1980 | Rosser et al. .................... 528/362 |
| 4,242,498 | 12/1980 | Rosser et al. . |
| 4,434,106 | 2/1984 | Rosser et al. .................... 528/401 |

FOREIGN PATENT DOCUMENTS

| | | |
|---|---|---|
| A-0432273 | 6/1991 | European Pat. Off. . |
| 2-202919 | 3/1990 | Japan . |
| 4-85328 | 3/1992 | Japan . |
| 5-78478 | 3/1993 | Japan . |

OTHER PUBLICATIONS

Fukui et al., Translation of JP 4-85328 Mar. 1992.
Ikeda et al., Translation of JP 5-78478 Mar., 1993.
Journal of Polymer Science: Polymer Letters Edition, vol. 18, pp. 135-139 (1980) John Wiley & Sons, Inc.
Ind. Eng. Chem. Product Research Development, vol. 20, pp. 694-696 (1981) American Chemical Society.
Japanese Industrial Standard (JIS), K 2220 (1984) Japanese Standards Association.
T.S. Croft et al. 'Perfluoroalkyl Ether Di-s-triazinyl Substituted Alkanes' Industrial & Engineering Chemistry—Product Research and Development, vol. 13, No. 2, Jun. 1974, pp. 144-147.
R.A. Korus 'High Performance Perfluoroalkyl Ether Triazine Elastomers' Industrial Engineering Chemistry—Product Research and Development, vol. 20, No. 4, Dec. 1981, pp. 694-696.
R.W. Rosser et al. 'synthesis of perfluoroalkylether triazine elastomers' Journal of Polymer Science: Polymer Letters Edition, vol. 18, 1980, pp. 135-139.

*Primary Examiner*—Jeffrey C. Mullis
*Attorney, Agent, or Firm*—Barnes & Thornburg

[57] ABSTRACT

Perfluoroalkyleneethertriazine oligomer obtained by reacting a dinitrile compound NC—Ff$^o$—CN, where Ff$^o$ is —(CFXOCF$_2$)a(CF$_2$)b(CF$_2$OCFX)c—, where X is a fluorine atom or a CF$_3$ group, a is an integer of 1 to 5, b is an integer of 1 to 2 and c is an integer of 1 to 5, or Rf$^o$ is —CF$_2$O(CF$_2$O)dCF$_2$—, where d is an integer of 1 to 8, with ammonia, further reacting the resulting diamizine compound with a dinitrile compound NC—Rf$^1$—CN, Rf$^1$ has the same meaning as that for Rf$^o$ or Rf$^1$ is a perfluoroalkylene group having 4 to 8 carbon atoms thereby obtaining a perfluoroalkyleneetherpolyimidoylamizine oligomer, then reacting the resulting oligomer with a perfluoronitrile compound Rf$^2$CN, Rf$^2$ is CF$_3$(OCF$_2$)$_e$— where e is an integer of 3 to 10 thereby treating the terminal groups thereof, and then subjecting the resulting terminal-treated oligomer to a ring-closing reaction with a perfluoroacylating agent RF$^3$COY, Rf$^3$ is CF$_3$(OCF$_2$)$_f$— where f is an integer of 3 to 10 has a good resistance to oxidation in the presence of a metal at a high temperature, and can improve the heat resistance of a perfluoropolyetherpolytetrafluoroethylene powder-based grease, when added therto.

3 Claims, No Drawings

PERFLUOROALKYLENEETHERTRIAZINE OLIGOMER AND PROCESS FOR PRODUCING THE SAME

BACKGROUND OF THE INVENTION

1. Field of the Invention

The present invention relates to a perfluoroalkyleneethertriazine oligomer and a process for producing the same, and more particularly an oily perfluoroalkyleneethertriazine oligomer useful as an effective oxidation stabilizer for greases, vacuum pump oils, etc. and a process for producing the same.

2. Description of the Prior Art

Liquid perfluoropolyether has a good resistance to heat and oxidation, and also has good lubricability and non-flammability. However, it undergoes a thermal oxidation-type decomposition at a temperature of 250° C. or higher, where the decomposition is accelerated in the presence of some metal or oxide thereof, and the resulting decomposition product gives rise to metal corrosion.

The resistance of liquid perfluoropolyether to oxidation in the presence of such a metal at a high temperature can be increased with an additive capable of inhibiting progress of metal corrosion process. It is also known that a good result can be obtained by using an aromatic phosphine and a phosphorus-containing triazine as oxidation-resistant, corrosion-resistant additives. However, these additives still have drawbacks, i.e. a relatively large volatility at a high temperature and a low solubility in perfluoropolyether at room temperature or a lower temperature.

Another class of liquids particularly stable for the thermal oxidation includes a liquid perfluorotriazine. A fluorine-containing, symmetric triazine has a high stability against the thermal oxidation even at 343° C., but undergoes complete evaporation at 204° C. over 6.5 hours due to the low molecular weight. It is also known that $\alpha,\omega$-di(symmetric triazinyl)perfluoroalkanes having various structures have a good stability against the thermal oxidation, but undergo considerable evaporation at a higher temperature than 200° C. also due to a relatively low molecular weights, and thus have not yet been utilized as a lubricant additive or in other applications.

SUMMARY OF THE INVENTION

An object of the present invention is to provide a perfluoroalkyleneethertriazine oligomer having a good resistance to oxidation in the presence of a metal at a high temperature and capable of improving the heat resistance of perfluoropolyether-based oil or perfluoropolyetherpolytetrafluoroethylene powder-based grease, when added thereto.

According to the present invention, there is provided a perfluoroalkyleneethertriazine oligomer represented by the following general formula:

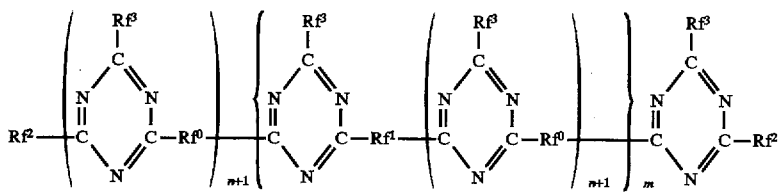

wherein $Rf^o$ is $-(CFXOCF_2)a(CF_2)b(CF_2OCFX)c-$, where X is a fluorine atom or a $CF_3$ group, a is an integer of 1 to 5, b is an integer of 1 to 2 and c is an integer of 1 to 5, or $Rf^o$ is $-CF_2O(CF_2O)dCF_2-$, where d is an integer of 1 to 8; $Rf^1$ has the same meaning as that for $Rf^o$ or a perfluoroalkylene group having 4 to 8 carbon atoms; $Rf^2$ is a perfluoroalkyl group having 1 to 8 carbon atoms, $CF_3(OCF_2)e-$, where e is an integer of 3 to 10, or $RfO(CFXCF_2O)kCFX-$, where Rf is a perfluoro(lower alkyl) group, X is a fluorine atom or a $CF_3$ group, and k is an integer of 1 to 8; and $Rf^3$ is $Rf(OCFX)f-$, where Rf is a perfluoroalkyl group having 1 to 8 carbon atoms, X is a fluorine atom or a $CF_3$ group, and f is an integer of 3 to 10, and n is 0.01 to 10 and m is 0.01 to 20.

The present perfluoroalkyleneethertriazine oligomer can be produced according to a series of the following steps, where $Rf^o$, $Rf^2$, $Rf^3$, $Rf^3$ and n and m in the general formula for starting materials and intermediate products have the same meanings as defined above.

First step

Dinitrile compound represented by the general formula $NC-Rf^o-CN$ is subjected to reaction with ammonia to obtain a diamizine compound [I] represented by the following general formula:

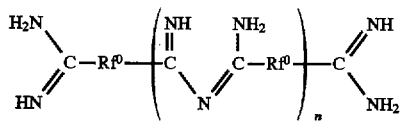

Dinitrile compound for use in the present invention includes compounds [V] whose $Rf^o$ is $-(CFXOCF_2)a(CF_2)b(CF_2OCFX)c-$, for example, $NCCF_2OCF_2CF_2CF_2OCF_2CN$, $NCCF_2OCF_2CF_2CF_2CF_2OCF_2CN$, $NCCF(CF_3)OCF_2CF_2CF_2OCF(CF_3)CN$, $NC[CF(CF_3)OCF_2]_2CF_2CF_2OCF(CF_3)CN$, $NC[CF(CF_3)OCF_2]_2CF_2[CF_2OCF(CF_3)]_2CN$ and $NC[CF(CF_3)OCF_2]_2CF_2[CF_2OCF(CF_3)]_2CN_2$, and compounds [VI] whose $Rf^o$ is $-CF_2O(CF_2O)dCF_2-$, for example, $NCCF_2OCF_2OCF_2CN$, $NCCF_2O(CF_2O)_3CF_2CN$, $NCCF_2O(CF_2O)_6CF_2CN$ and $NCCF_2O(CF_2O)_8CF_2CN$.

Among the compounds [V], compounds whose X is $CF_3$ can be produced by reacting the terminal groups of hexafluoropropeneoxide oligomer with alcohol to esterify the terminal groups, followed by reaction with ammonia, or by direct reaction of the terminal groups with ammonia to form an acid amide $H_2NOCRf^oCONH_2$, followed by dehydration reaction with a dehydrating agent such as phosphoric anhydride, perfluoroacetic anhydride or the like. Furthermore, among the compounds [V], compounds whose X is F can be produced by using a compound derived from perfluoroethyleneoxide oligomer as a starting compound and the compounds [VI] can be produced by using a compound derived from difluorooxymethylene oligomer as a starting compound, each followed by applying thereto the same terminal nitrilation reaction as described above.

Inevitably, the thus obtained dinitrile compounds contain mononitrile compounds as by-products. It is possible to suppress formation of mononitrile compounds by using starting materials, catalyst, solvent, etc. having a very high purity and conducting the reaction under restricted conditions, and dinitrile compounds having a high purity can be produced thereby. However, the production cost is considerably increased.

In the present invention, dinitrile compounds having a relatively low molecular weight can be used and thus starting materials and by-products can be readily separated therefrom by an appropriate purification means such as distillation, etc. and dinitrile compounds having a purity of 95% or more can be usually obtained. It is not particularly difficult to obtain a dinitrile compound having a purity of 98% or more. Number average molecular weight and bifunctional purity of dinitrile compound can be conveniently determined by $^{13}$F-NMR spectrum analysis.

Reaction of dinitrile compound with ammonia is carried out by carefully adding a dinitrile compound dropwise to generally at least 5 parts by mole, preferably 20 parts by mole, of ammonia per part by mole of the dinitrile compound with stirring. In case of using less than 5 parts by mole of ammonia, the reaction to form amizine groups is retarded and other side reactions occur considerably.

Generally, liquid ammonia is used as ammonia. Gaseous ammonia can be also used, where it is preferable to conduct the reaction under pressure by making the partial pressure of ammonia as high as possible. It is also possible to conduct the reaction while keeping ammonia in solution in a solvent, where ether-based solvents such as diethylether, tetrahydrofuran, etc.; hydrocarbon-based solvents such as cyclohexane, octane, toluene, etc., and chlorine-based solvents such as dichloromethane, dichloroethane, etc. can be used as the solvent. Fluorine-based solvents such as trichlorotrifluoroethane, perfluorohexane, perfluoroethane, perfluoro(2-butyltetrahydrofuran), 2H-tetradecafluoro-5-(trifluoromethyl)-3,6-dioxanonane, perfluorotributylamine, etc. or mixtures containing these solvents are particulary preferable owing to their high solubility of the respective starting materials.

Reaction temperature is in a range of about −90° C. to about +70° C., preferably about −70° C. to about +50° C. Below about −90° C., no substantial reaction rate can be obtained, whereas above about +70° C., the vapor pressure of ammonia is so high that reaction operations are hard to obtain. When the reaction temperature is below −33° C., boiling point of ammonia, any pressure vessel is not required for the reaction, whereas at a reaction temperature of −33° C. or higher, it is preferable to use a pressure vessel for the reaction. However, when a fluorine-based solvent having a good ammonia solubility, it is not always necessary to use a pressure vessel even at or above −33° C., but even in that case it is desirable to conduct the reaction in a pressure vessel at a high ammonia concentration condition.

As a result of reaction of dinitrile compound with ammonia, a reaction product containing a diamizine compound [I] having amizine groups converted from nitrile groups as the main component can be obtained. It has been confirmed by $^{13}$F-NMR spectrum analysis that a small amount of other terminal functional groups than the amizine groups are formed at the same time, but the reaction product itself can be used in the successive reaction. Since the nitrile groups of dinitrile compound have characteristic absorption at 2,260 cm$^{-1}$, whereas the amizine groups have a characteristic absorption at 1,695 cm$^{-1}$, the degree of reaction progress can be readily detected by changes in these peak intensities.

The resulting diamizine compound has n=0.01~4 in said formula [I].

Second step

The diamizine compound [I] obtained in the first step is further subjected to reaction with a dinitrile compound represented by the general formula NC—Rf$^1$—CN to obtain perfluoroalkyleneetherpolyimidoylamizine oligomer [II] represented by the following general formula:

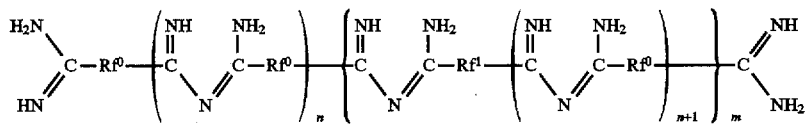

This reaction to polymerize the diamizine compound [I] is carried out under the substantially same conditions as in the first step, and in that case the diamizine compound must be used at least in an equimolar amount to the dinitrile compound. When more dinitrile compound is used, the CN groups will remain at the molecule terminals of the resulting perfluoroalkyleneetherpolyimidoylamizine oligomer [II], which will give an adverse effect to the reaction to treat the terminal groups to be carried out in the successive third step.

The degree of the third step reaction can be detected by measurement of infrared absorption spectrum or viscosity. As to the measurement of viscosity it is reported that there is a linear relationship between the weight average molecular weight by GPC of the oligomer and that of polytriazine derived therefrom [J. of Polymer Sci.; Polymer letters Ed. Vol. 18, page 135, (1980); Ind. Eng. Chem.; Product research development, Vol. 20, page 694 (1981); U.S. Pat. No. 4,242,498].

The process for producing perfluoroalkyleneetherpolyimidoylamizine oligomer based on the foregoing first and second steps can produce the product up to a considerable degree of polymerization by the two-stage polymerization procedure from a readily available dinitrile compound of relatively low molecular weight as a starting material.

Third step

The perfluoroalkyleneetherpolyimidoylamizine obtained in the second step is further subjected to reaction with a perfluoronitrile compound represented by the general formula Rf$^2$CN to obtain terminal group-treated perfluoroalkyleneetherpolyimidoylamizine oligomer [III] represented by the following general formula:

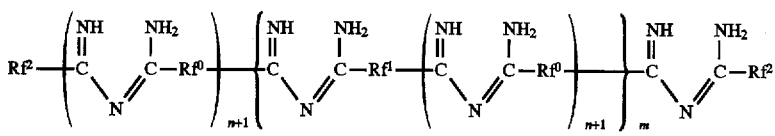

The perfluoronitrile compound for use in the present invention includes compounds [VII] whose $Rf^2$ is a perfluoroalkyl group, for example, $CF_3CN$, $C_2F_5CN$, $C_3F_7CN$, $C_6F_{13}CN$ and $C_6F_{17}CN$; compounds [VIII] whose $Rf^2$ is $CF_3(OCF_2)e—$, for example, $CF_3(OCF_2)_6CN$, $CF_3(OCF_2)_8CN$ and $CF_3(OCF_2)_9CN$; and compounds [IX] whose $Rf^2$ is $RfO(CFXCF_2O)kCFX—$, for example, $CF_3OCF_2CF_2OCF_2CN$, $CF_3O(CF_2CF_2O)_2CF_2CN$, $C_3F_7O(CF_2CF_2O)_3CF_2CN$, $CH_3OCF(CF_3)CF_2OCF(CF_3)CN$, $CH_3O[CF(CF_3)CF_2O]_2CF(CF_3)CN$, $CH_3O[CF(CF_3)CF_2O]_3CF(CF_3)CN$, $C_3F_7OCF(CF_3)CF_2CF(CF_3)CN$, $C_3F_7O[CF(CF_3)CF_2O]_2CF(CF_3)CN$ and $C_3F_7O[CF(CF_3)CF_2O_3]CF(CF_3)CN$.

The perfluoronitrile compound is usually used by about 10 to about 20% by mole in excess of the perfluoroalkyleneetherpolyimidoylamizine oligomer and the conditions for the third step reaction are substantially the same as those for the first step reaction.

Fourth step

The terminal group-treated perfluoroalkyleneetherpolyimidoylamizine oligomer [III] obtained in the third step is further subjected to a ring-closing reaction with a perfluoroacylating agent represented by the general formula $Rf^3COY$, where Y is a halogen atom, to obtain the desired perfluoroalkyleneethertriazine oligomer [IV].

The perfluoroacylating agent for use in the present invention includes, for example, $CF_3(OCF_2)_5COF$, $CF_3(OCF_2)_6COF$, $CF_3(OCF_2)_7COF$, $CF_3(OCF_2)_8COF$, $CF_3(OCF_2)_9COF$, $C_2F_5(OCF_2)_8COF$, $C_3F_7(OCF_2)_5COF$ and $CF_3[OCF(CF_3)]_3COF$. The ring-closing reaction with the perfluoroacelating agent is usually carried out in the presence of a tertiary amine such as pyridine, aromatic amines, etc.

After the end of reaction, the resulting reaction product is added to chloroform, and the chloroform-insoluble layer is separated therefrom. An oxygen-containing gas, preferably air, is blown into the remaining liquid compound at about 250° to about 350° C., preferably about 300° to about 320° C. to remove impurities therefrom. Then, the resulting liquid compound is subjected to purification (decolorization and clarifying) with an adsorbent such as activated carbon, silica, alumina, etc., preferably wet process silica.

The resulting perfluoroalkyleneethertriazine oligomer [IV] is added to perfluoropolyether having a viscosity of about 10 to about 500 Cst at 40° C., represented by anyone of the following general formula (a), (b), (c) and (d):

(a) $Rf^4O(CFXC_2O)pRF^5$ wherein $Rf^4$ and $Rf^5$ are perfluoro(lower alkyl) groups; X is a fluorine atom or a $CF_3$ group; and p is an integer of 10 to 100, (b) $Rf^4O(CF_2CF_2CF_2O)pRF^5$ wherein $Rf^4$, $Rf^3$ and p have the same meanings as defined above, (c) $Rf^6O(CFXCF_2O)q(CF_2O)rRf^7$ wherein $Rf^6$ and $Rf^7$ are perfluoro(lower alkyl) groups; X has the same meaning as defined above; q is 99.9 to 90; and r is 0.1 to 10, and (d) $Rf^6O(CF_2CF_2O)s(CF_2O)tRf^7$ wherein $Rf^6$, $Rf^7$ have the same meanings as defined above; s is 90 to 30 and t is 20 to 3, where s/t is (90–80)/(10–20), and can form an oily composition with an improved heat resistance. In that case, about 20 to about 5 parts by weight of perfluoroalkyleneethertriazine oligomer [IV] is added to about 80 to about 95 parts by weight of oil consisting of perfluoropolyether.

Furthermore, a greasy composition with an improved heat resistance can be obtained by adding about 5 to about 60 parts by weight, preferably about 15 to about 45 parts by weight, of polytetrafluoroethylene powder to 100 parts by weight of the above oily composition.

The present invention provides a perfluoroalkyleneethertriazine oligomer having a good resistance to oxidation at a high temperature, particularly at a high temperature in the presence of a metal, and can improve the heat resistance of a perfluoropolyether-based oil or a perfluoropolyetherpolytetrafluoroethylene powder-based grease, when added thereto. Furthermore, the present perfluoroalkyleneethertriazine oligomer is also distinguished in the cryogenic resistance, since it has perfluoropolyether groups at the side chains.

PREFERRED EMBODIMENTS OF THE INVENTION

The present invention will be described in detail below, referring to Examples.

EXAMPLE 1

(1) Synthesis of diamizine compound:

A flask having a capacity of 0.25 liters, provided with a granular KOH-filled, ammonia inlet tube, a stirrer, a thermometer and a reflux condenser (dry ice/ethanol) was cooled over a dry ice/ethanol bath, and then 39.1 g (2.3 moles) of dry ammonia was introduced therein through the ammonia inlet tube. After the above-mentioned amount of the ammonia as liquefied was introduced into the flask, the ammonia inlet tube was replaced with a dropping funnel, and 50 g (0.115 moles) of dinitrile compound having the following formula:

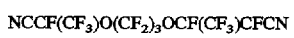

$NCCF(CF_3)O(CF_2)_3OCF(CF_3)CFCN$ was carefully dropwise added thereto with stirring, while maintaining the inside temperature at $-60°$ C. to $-70°$ C. After the dropwise addition, stirring was further continued for 0.5 hours at that temperature.

Then, the reaction system was brought back to the ordinary temperature and the atmospheric pressure, and unreacted ammmonia gas was purged therefrom, and then the reaction system was heated at 40° C. under reduced pressure (about 1 to 3 mmHg) for about 6 hours, whereby 48.0 g of diamizine compound having a molecular weight of 766 ($[\eta]=0.66$) and the following structural formula was obtained (yield: 54.5%).

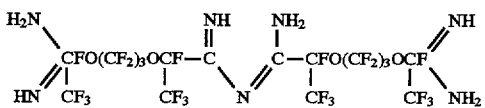

(2) Synthesis of perfluoroalkyleneetherpolyimidoylamizine oliopmer:

46.3 g (0.06 moles) of the thus obtained diamizine compound and 21.6 g (0.05 moles) of the same dinitrile compound as used above (1) were charged into a 4-necked flask having a capacity of 200 ml, provided with a stirrer, a thermometer, a reflux condenser and an inert gas line connection, and stirred for 6 hours, while maintaining the flask at a temperature of 25° to 30° C., whereby 68 g of perfluoroalkyleneetherpolyimidoylamizine oligomer having a molecular weight of 11,450 (by isoplestic measurement in perfluorobenzene, as will be here after used for the measurement of molecular weight) was obtained (yield: 99%).

(3) Synthesis of terminal group-treated perfluoroalkyleneetherpolyimidoylamizine oligomer:

8.9 g (0.019 moles) of $CF_3(CF_2)_5CN$ was added to the perfluoroalkyleneetherpolyimidoylamizine oligomer obtained in (2) and the mixture was stirred for 3 hours, while keeping the flask at a temperature of 25° to 30° C., whereby 72.1 g of the terminal groups-stabilized perfluoroalkyleneetherpolyimidoylamizine oligomer having a molecular weight of 12,140 was obtained (yield: 99.8%).

(4) Synthesis of perfluoroalkyleneethertriazine oligomer:

40.9 g (0.518 moles) of dry pyridine, 100 ml of dry Freon 113 and 195.7 g (0.382 moles) of $CF_3(OCF_2)_6COF$ were charged into a 5-necked flask having a capacity of 500 ml, provided with a stirrer, a reflux cooler, a thermometer, a dropping funnel and an inert gas inlet tube, and then 72.1 g (0.16 moles) of the terminal group-treated perfluoroalkyleneetherpolyimidoylamizine oligomer obtained in (3) and dissolved in dry Fron was dropwise added thereto with stirring. After the dropwise addition, stirring was further continued for 6 hours, while keeping the flask at a temperature of 40° to 45° C. After the reaction mixture was cooled, 300 ml of chloroform was added thereto, and the resulting chloroform-insoluble layer was separated. The separated layer was washed three times with 200 ml of chloroform.

The resulting liquid compound was transferred into a flask connected to a receptacle, and dry air was bubbled in the flask for 12 hours, while heating the flask at a temperature of 300° to 310° C. After the cooling, the liquid compound was placed on a filter under pressure, and 8.0 g of wet process silica was added thereto with stirring. The mixture was filtered through a filter paper under pressure, whereby 105.0 g of liquid perfluoroalkyleneethertriazine oligomer having a molecular weight of 23,700 was obtained (yield: 69.5%).

Kinematic viscosity (50° C.): 262 mm²/sec.

Solidification point: –40° C.

Heating loss (in air at 300° C. for 31 hours): 13.2%

EXAMPLES 2 to 14

Perfluoroalkyleneethertriazine oligomers represented by the following general formula:

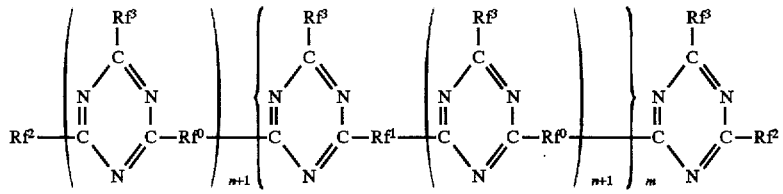

were produced through a series of the same steps as in Example 1.

In the foregoing general formula, groups $Rf^0$, $Rf^1$, $Rf^2$ and $Rf^3$ are shown in the following Table 1.

TABLE 1

| Ex. No. | $Rf^0$ | $Rf^1$ | $Rf^2$ | $Rf^3$ |
|---|---|---|---|---|
| 1 | —(A)CF$_2$(B)— | —(A)CF$_2$(B)— | $C_6F_{13}$— | $CF_3(OCF_2)_6$— |
| 2 | —(A)$_3$CF$_2$(B)$_2$— | —(A)$_3$CF$_2$(B)$_2$— | " | $CF_3(OCF_2)_{6.5}$— |
| 3 | " | " | " | $CF_3(OCF_2)_{8.2}$— |
| 4 | " | —(CF$_2$)$_6$— | " | $CF_3(OCF_2)_6$— |
| 5 | " | " | " | " |
| 6 | " | —(A)CF$_2$(B)— | " | " |
| 7 | —(A)$_2$CF$_2$(B)$_2$— | —(A)$_2$CF$_2$(B)$_2$ | $CF_3(OCF_2)_3$— | $CF_3(OCF)_{8.7}$— |
| 8 | " | " | " | $CF_3(OCF_2)_8$— |
| 9 | " | " | " | $CF_3(OCF_2)_9$— |
| 10 | " | " | $CF_3(OCF_2)_{8.5}$— | $CF_3(OCF_2)_8$— |
| 11 | —(A)CF$_2$(B)— | (A)CF$_2$(B)— | $CF_3(OCF_2)_6$— | $CF_3(OCF_2)_6$— |
| 12 | " | " | " | " |
| 13 | —(A)$_2$CF$_2$(B)— | " | $CF_3(OCF_2)_9$— | $CF_3(OCF_2)_7$— |
| 14 | " | " | $CF_3(OCF_2)_8$— | $CF_3(OCF_2)_8$— |

Remarks:

(A): 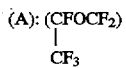

(B): 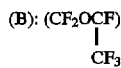

The liquid perfluoroalkyleneethertriazine oligomers obtained in Examples 2 to 14 were measured for the following properties:

| | |
|---|---|
| n value: | (diamizine MW − $Rf^0$ dinitrile Mw − 34)/ ($Rf^0$ dinitrile MW + 17) |
| m value: | [(oligomer MW) − (n + 1)($Rf^1$ dinitrile MW) − (n + 2)($Rf^3$COY MW − 21) − 2($Rf^2$ dinitrile MW)]/ [(n + 1)($Rf^1$ dinitrile MW) + ($Rf^0$ dinitrile MW) + (n + 2)($Rf^3$COY MW − 21)] |

Diamine/dinitrile ratio (DA/DN ratio)
Found number average molecular weight (found Mn)
Yield (%)
Kinematic viscosity (50° C., $mm^2$/sec.): by Canon-Fenske viscometer
Solidification point (°C.)
Amount of volatile matters by heating in air (% by weight): heating at 300° C. for one hour, 300° C. for 31 hours and 350° C. for one hour
Heating loss (% by weight): heating at 300° C. for 620 hours, 800 hours or 1,000 hours.
The results are showing in the following Table 2.

Separately, a greasy composition [B] was prepared from 670 g of the above-mentioned perfluoropolyether and 330 g of the polytetrafluoroethylene powder without using the perfluoroalkyleneethertriazine oligomer.

These greasy compositions were measured for the following properties and the results are shown in the following Table 3.

Liquation consistency: according to JIS K-2220
Evaporation amount: weight loss of greasy composition, when 0.6 g of greasy composition was uniformly applied to an aluminum dish, having 35 mm in diameter and 5 mm deep, followed by heating at 300° C. for 5 hours, 50 hours or 300 hours

TABLE 3

| Greasy composition | Liquation consistency | Evaporation amount (wt. %) | | |
|---|---|---|---|---|
| | | 5 hrs | 50 hrs | 300 hrs |
| A | 270 | 5.3 | 9.2 | 13.7 |
| B | 265 | 25.9 | 55.2 | 60.4 |

TABLE 2

| Properties\Example No. | 1 | 2 | 3 | 4 | 5 | 6 | 7 |
|---|---|---|---|---|---|---|---|
| n value | 0.625 | 0.098 | 0.098 | 0.210 | 0.210 | 0.210 | 0.237 |
| m value | 9.81 | 9.06 | 9.87 | 4.34 | 5.53 | 6.05 | 1.81 |
| DA/DN ratio | 1.125 | 1.125 | 1.125 | 1.333 | 1.333 | 1.333 | 1.500 |
| Found Mn | 23700 | 28400 | 32200 | 11630 | 14290 | 16130 | 8600 |
| Yield | 70.0 | 75.5 | 74.8 | 78.0 | 82.0 | 71.9 | 81.2 |
| Kinematic viscosity | 262 | 1098 | 888 | 143 | 285 | 509 | 58 |
| Solidification point | −40 | −35 | −40 | −52 | −48 | −49 | −67 |
| Amount of volatile matters | | | | | | | |
| 300° C.-1 hr | 5.6 | 4.1 | 0.8 | 22.8 | 19.7 | 17.3 | 28.4 |
| 300° C.-31 hrs | 15.0 | 10.0 | 7.2 | | | | 56.5 |
| 350° C.-1 hr | 14.3 | 7.8 | 5.6 | | | | |
| Heating loss | | | | | | | |
| 620 hrs | | | | | | | |
| 800 hrs | | | | | | | 41.6 |
| 1000 hrs | 9.9 | 6.3 | 3.6 | 28.9 | 17.6 | 9.9 | |

| Properties\Example No. | 8 | 9 | 10 | 11 | 12 | 13 | 14 |
|---|---|---|---|---|---|---|---|
| n value | 0.237 | 0.237 | 7.310 | 0.082 | 0.082 | 0.070 | 0.120 |
| m value | 2.60 | 4.00 | 0.16 | 3.41 | 5.29 | 2.86 | 5.35 |
| DA/DN ratio | 1.333 | 1.250 | — | 1.500 | 1.200 | 1.220 | 1.220 |
| Found Mn | 11000 | 15800 | 14500 | 8140 | 11360 | 9070 | 12690 |
| Yield | 75.4 | 86.0 | 83.0 | 67.0 | 71.6 | 74.0 | 71.0 |
| Kinematic viscosity | 125 | 108 | 129 | 57 | 110 | 88 | 138 |
| Solidification point | −58 | −67 | −63 | −68 | −60 | −72 | −61 |
| Amount of volatile matters | | | | | | | |
| 300° C.-1 hr | 20.3 | 10.7 | 17.3 | 34.4 | 20.6 | 20.8 | 12.6 |
| 300° C.-31 hr | 38.3 | 29.0 | 32.4 | 52.6 | 32.7 | 48.6 | 33.6 |
| 350° C.-1 hr | | | | | | | |
| Heating loss | | | | | | | |
| 620 hrs | | | | | | 5.8 | 4.3 |
| 800 hrs | 30.7 | 18.5 | 23.4 | | | | |
| 1000 hrs | | | | 30.6 | 22.0 | | |

To 50 g of the perfluoroalkyleneethertriazine oligomer obtained in Example 3 were added the following materials:
$C_3F_7O[CF(CF_3)CF_2O]q(CF_2O)rCF_3$: 620 g
q:r=97:3
viscosity: 330 $mm^2$/sec. (40° C.)
Polytetrafluoroethylene powder: 330 g
Then, the mixture was stirred in a stirring vessel for one hour and kneaded through rolls at three stages to obtain a greasy mixture [A].

It is obvious from Table 3 that the present greasy composition has a good stability against oxidation at a high temperature even in the presence of a metal.

EXAMPLE 15 to 29

Other perfluoroalkyleneethertriazine oligomers having the following general formula were synthesized through a series of he same steps as in Example 1.

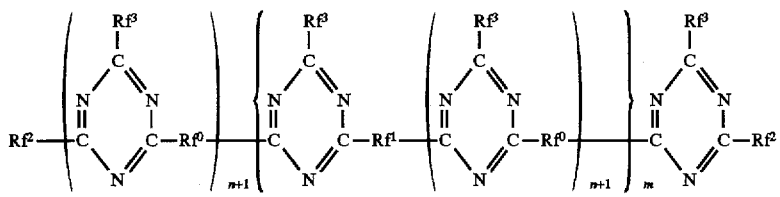

In the general formula, groups $Rf^0$, $Rf^1$, $Rf^2$ and $Rf^3$ are shown in the following Table 4.

TABLE 4

| Ex. No. | $Rf^0$, $Rf^1$ | $Rf^2$ | $Rf^3$ |
|---|---|---|---|
| 15 | —(A)₃CF₂(B)₃— | C₃F₇O(D)— | CF₃(OCH₂)₆— |
| 16 | " | CF₃(OCH₂)₈— | " |
| 17 | " | " | " |
| 18 | " | C₃F₇O(D)— | CF₃(OCF₂)₈— |
| 19 | " | " | " |
| 20 | " | CF₃(OCF₂)₈— | " |
| 21 | —(A)CF₂(B)— | C₃F₇O(D)— | CF₃(OCF₂)₆— |
| 22 | " | " | " |
| 23 | " | CF₃(OCF₂)₈— | " |
| 24 | " | C₃F₇O(D)— | CF₃(OCF₂)₈— |
| 25 | " | " | " |
| 26 | " | CF₃(OCF₂)₈— | " |
| 27 | —CF₂O(CF₂O)₆CF₂— | " | " |
| 28 | " | " | " |
| 29 | " | " | " |

Remarks:

(A): 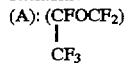

(B): 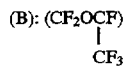

(D): 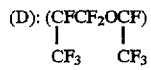

The liquid perfluoroalkyleneethertriazine oligomers obtained in Examples 15 to 29 had properties given in the following Table 5.

TABLE 5

| Ex. No. | Found Mn | Kinematic viscosity | Solidification point |
|---|---|---|---|
| 15 | 10606 | 525 | −35 |
| 16 | 8330 | 139 | −55 |
| 17 | 15450 | 598 | −41 |
| 18 | 8930 | 173 | −54 |
| 19 | 15850 | 712 | −44 |
| 20 | 10300 | 107 | −65 |
| 21 | 8750 | 143 | −53 |
| 22 | 13090 | 306 | −50 |
| 23 | 11310 | 140 | −65 |
| 24 | 9435 | 102 | −63 |
| 25 | 12680 | 186 | −61 |
| 26 | 10090 | 93 | −77 |
| 27 | 9000 | — | −97 |
| 28 | 10000 | — | −94 |
| 29 | 12000 | — | −90 |

EXAMPLE 30

(1) About 0.3 g of perfluoroalkyleneethertriazine oligomer obtained in Example 3 was placed on an aluminum dish, having 30 mm in diameter and 7 mm deep, and then exactly weighted. Then, the dish was placed in an oven at 300° C. After 5 hours, weight loss was measured. It was found to be 3. 93%.

(2) Weight loss of CF₃O[CF(CF₃)CF₂O]q(CF₂O)rC₂F₅, where q:r=98:2; viscosity: 150 mm²/sec. (40° C.) and 45 mm²/sec. (100° C.); and solidification point: −70° C., was measured in the same manner as in (1) and was found to be 85.1%.

(3) Weight loss of an oily mixture consisting of 95 parts by weight of the same perfluoropolyether ae used in (2) and 5 parts by weight of the same perfluoroalkyleneethertriazine oligomer as used in (1) was likewise measured and found to be 2.57%.

As is evident from the above, the present perfluoroalkyleneethertriazine oligomer can effectively prevent decomposition due to a metal, as often observed in case of perfluoropolyether.

What is claimed is:

1. A process for producing a perfluoroalkyleneethertriazine oligomer represented by the following general formula:

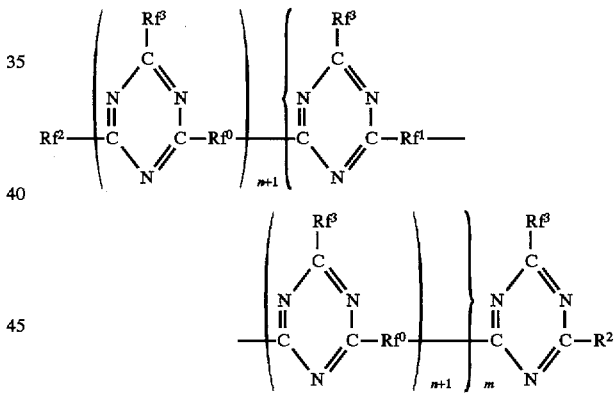

wherein $Rf^0$ is —(CFXOCF₂)a(CF₂)b(CF₂OCFX)c—, where X is a fluorine atom or a CF₃ group, a is an integer of 1 to 5, b is an integer of 1 to 2 and c is an integer of 1 to 5, or $Rf^0$ is —CF₂O(CF₂O)dCF₂—, where d is an integer of 1 to 8; $Rf^1$ has the same meaning as that for $Rf^0$ or $Rf^1$ is a perfluoroalkylene group having 4 to 8 carbon atoms; $Rf^2$ is CF₃(OCF₂)ₑ— where e is an integer of 3 to 10; and $Rf^3$ is CF₃(OCF₂)f, where f is an integer of 3 to 10 and n is 0.01 to 10 and m is 0.01 to 20, which comprises subjecting a terminally treated perfluoroalkyleneetherpolyimidoylamizine oligomer represented by the following general formula:

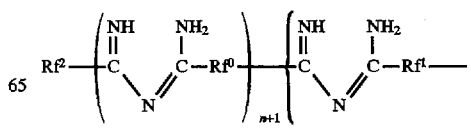

-continued

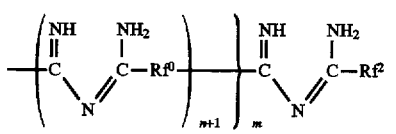

wherein $Rf^0$, $Rf^1$, $Rf^2$, n and m have the same meanings as above, to a ring-closing reaction with a perfluoroacylating agent represented by the general formula: $Rf^3COY$, wherein $Rf^3$ has the same meaning as defined above, and Y is a halogen atom.

2. A process according to claim 1, wherein an oxygen-containing gas is blown into the resulting ring-closing reaction product at about 250° C. to about 350° C., thereby removing impurities therefrom, followed by purification treatment in the presence of a adsorbent.

3. A process according to claim 2, wherein the adsorbent is wet processed silica.

* * * * *